(12) United States Patent
McGhie (10) Patent No.: US 10,299,781 B2
(45) Date of Patent: May 28, 2019

(54) SUTURE RETENTION DEVICE

(71) Applicant: Cook Medical Technologies LLC, Bloomington, IN (US)

(72) Inventor: Thomas W. McGhie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 208 days.

(21) Appl. No.: 15/285,590

(22) Filed: Oct. 5, 2016

(65) Prior Publication Data

US 2017/0095246 A1  Apr. 6, 2017

Related U.S. Application Data

(60) Provisional application No. 62/237,053, filed on Oct. 5, 2015.

(51) Int. Cl.
*A61B 17/04* (2006.01)

(52) U.S. Cl.
CPC .. *A61B 17/0401* (2013.01); *A61B 2017/0404* (2013.01); *A61B 2017/0417* (2013.01); *A61B 2017/0448* (2013.01); *A61B 2017/0464* (2013.01); *A61B 2017/0496* (2013.01)

(58) Field of Classification Search
CPC ...... F16G 11/04; F16G 11/044; F16G 11/046; F16G 11/00; F16G 11/03; F16G 11/10; F16G 11/103; F16G 11/105; E04C 5/12; E04C 5/122; E04C 5/125; D06F 53/00; D06F 53/005; A61B 17/0401; A61B 2017/0404; A61B 2017/0406; A61B 2017/0408; A61B 2017/0403; A61B 2017/0409; A61B 2017/0414; A61B 2017/0416; A61B 2017/0446; A61B 2017/0448; A61B 2017/045; A61B 2017/0451; A61B 2017/0454; A61B 2017/0459; A61B 2017/0461; A61B 2017/0462; A61B 2017/0496; A61B 2017/0464; A61B 2017/0417
USPC ....................................................... 24/115 R
See application file for complete search history.

(56) References Cited

U.S. PATENT DOCUMENTS

| 2,075,508 A | 7/1934 | Davidson |
| 3,976,079 A | 8/1976 | Samuels et al. |
| 4,969,892 A * | 11/1990 | Burton ............... A61B 17/0401 606/148 |
| 5,518,504 A * | 5/1996 | Polyak .................. A61F 2/0036 128/DIG. 25 |
| 8,540,740 B2 | 9/2013 | Lam et al. |
| 8,945,181 B2 | 2/2015 | Taylor et al. |

(Continued)

*Primary Examiner* — David C Eastwood
(74) *Attorney, Agent, or Firm* — Kevin L. Leffel (57) ABSTRACT

A suture retention device is described. The suture retention device has various uses, one being for a gastropexy. A gastropexy may use a suture to hold the stomach against the abdominal wall of a patient. According to one example, a suture retention device is described that may have a shell having a thickness and an upper surface and a lower surface spaced apart by the thickness, the shell having an outer diameter that is greater than the thickness, the shell defining an internal chamber. A spring may be mounted within the internal chamber. The shell may be movable relative to a suture that passes through the shell and engages the spring.

17 Claims, 9 Drawing Sheets

(56) References Cited

U.S. PATENT DOCUMENTS

2007/0073342 A1* 3/2007 Stone ................. A61B 17/0057
606/232
2014/0031864 A1 1/2014 Jafari et al.

* cited by examiner

SUTURE RETENTION DEVICE

CROSS REFERENCE TO RELATED APPLICATIONS

This application claims benefit of 62/237,053 filed on Oct. 5, 2015 entitled "SUTURE RETENTION DEVICE" the entire contents of which are incorporated herein by reference.

TECHNICAL FIELD

A suture retention device is described. The suture retention device has various uses, one being for a gastropexy. A gastropexy may use a suture to hold the stomach against the abdominal wall of a patient.

SUMMARY OF THE INVENTION

According to one example, a suture retention device is described that may have a shell having a thickness and an upper surface and a lower surface spaced apart by the thickness, the shell having an outer diameter that is greater than the thickness, the shell defining an internal chamber. A spring may be mounted within the internal chamber. The shell may be movable relative to a suture that passes through the shell and engages the spring.

DETAILED DESCRIPTION

Figure 1:
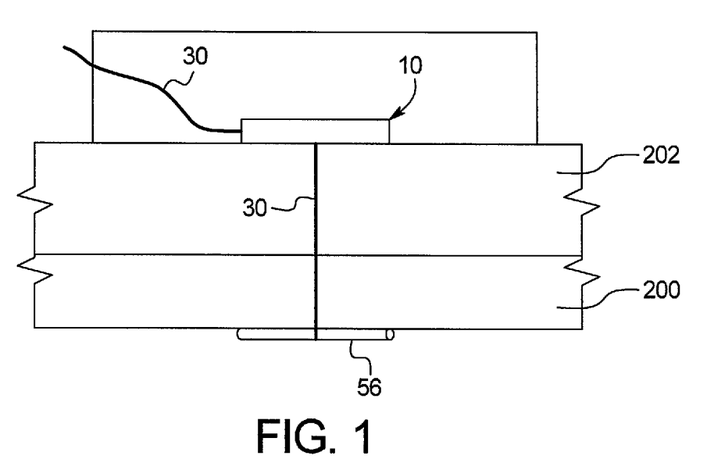
FIG. 1 presents a cross-sectional view of a gastropexy.

Various aspects of examples are presented in FIGS. 1-13, which are not drawn to any particular scale, and wherein similar components in the numerous views are numbered alike. FIG. 1 presents a gastropexy. A suture 30 is held in tension between a suture retention device 10 and an anchor 56. The anchor may take a variety forms. A common form is a short piece of metal wire or cannula with the suture attached at a mid-point. The anchor 56 could also be formed from plastic. The tension pulls the stomach 200 against the abdominal wall 202 of a patient. This allows an efficient percutaneous insertion of a feeding tube for example. The tension in the suture is what holds the stomach 200 against the abdominal wall 202 and the suture retention device 10 locks and holds the suture in place and under tension. Many dynamic conditions may be experienced by the system during the use of the device, for example the patient may stand, sit, or develop ascites. A rigid connection prohibits the system from responding to dynamic conditions, and may contribute to ulcers, especially at the skin surface. The example disclosed herein allows for resilience instead of a rigid connection.

Figure 2:
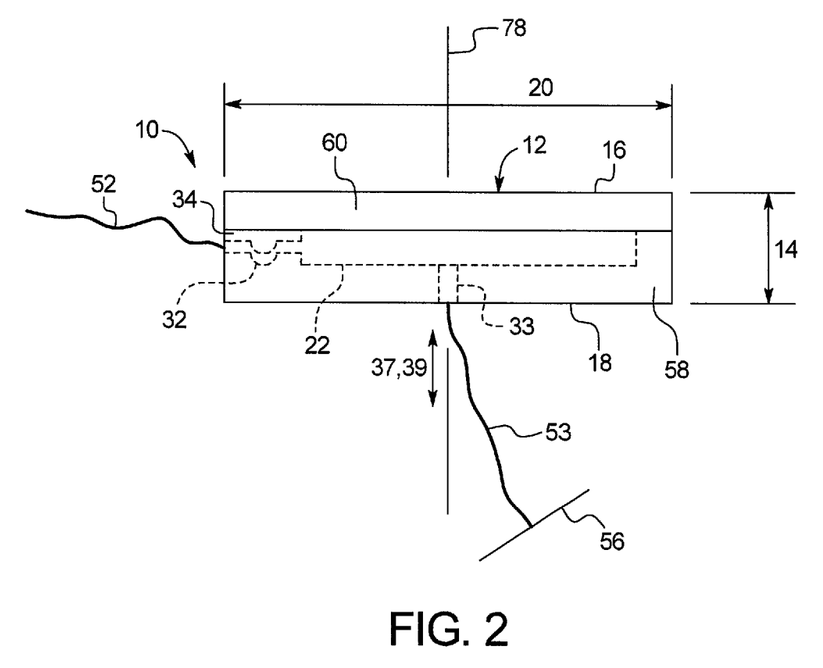
FIG. 2 presents a cross-sectional view of a suture retention device according one example in a locked configuration.

FIG. 2 presents a side view of the suture retention device 10 according to one example. A shell 12 has a thickness 14 and an upper surface 16 and a lower surface 18 spaced apart by the thickness 14. The shell 12 has an outer diameter 20 that is greater than the thickness 14, for example a flat, thin round object such as a disk. The shell may take other shapes, for example an oval, a polygon, or a square with rounded corners. These examples are not exhaustive as other shapes are possible. The diameter of a shell is the length of a straight line passing the furthest distance from side to side of the lower surface 18 through its center. In a square, for example, the diameter is the distance between opposite corners.

Furthermore the shell need not be exactly flat. For example one or both of the upper surface 16 and lower surface 18 may be curved, concave, or convex, or a combination of two or more of curved, concave and convex. The shell 12 defines an internal chamber 22. The lower surface 18 may have a suture entrance hole 33 through its center into the internal chamber 22.

In one example, the shell 12 comprises a lower body 58 and a mating cap 60 that covers the internal chamber 22.

Figure 3:
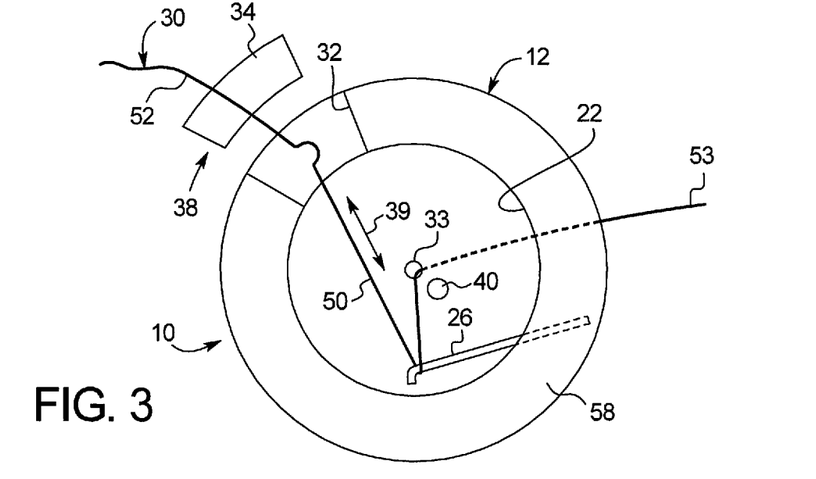
FIG. 3 is a top plan view of the FIG. 2 example without a cap in an unlocked configuration.
Figure 4:
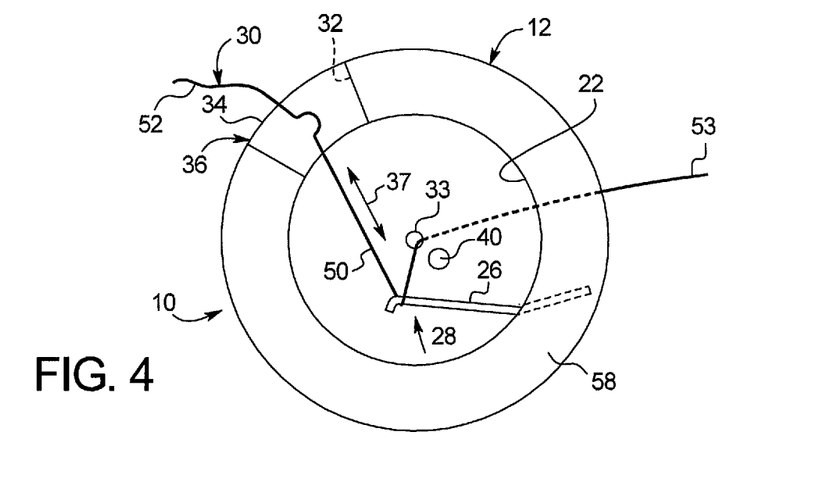
FIG. 4 is a top plan view without a cap showing the FIG. 3 example in a locked configuration.

Referring now to FIGS. 3 and 4, a spring 26 is mounted within the internal chamber 22 configured to apply a force to the suture 30 upon deflection 28. The suture retention device 10 has a locked configuration wherein the suture 30 passes through a suture exit hole 32 and in contact with the spring 26 and passes through a suture entrance hole 33 such that tension applied to the suture 30 causes the suture 30 to deflect 28 the spring 26. The suture may be locked to the shell 12 at the suture exit hole 32. The suture 30 may slide over the spring 26. The suture retention device 10 also has an unlocked configuration 38 that allows the shell 12 to freely move in either unlocked direction 39 along the suture 30 as shown in FIG. 3. The suture retention device 10 is free to move relative to the suture 30 without restraint. The suture retention device 10 is free to move to any location along the suture 30.

As shown in FIG. 4, when at a desired location, the suture lock 34 is put into place to lock the suture retention device 10 at the desired location. A suture lock 34 is connected to the shell 12, wherein the suture lock 34 has a locked configuration 36 that locks the suture 30 relative to the shell 12 while the spring 26 permits resilient movement of the shell 12 relative to the suture 30 in either locked direction 37 along the suture 30 under tension of the spring 26. The suture lock 34 may be configured to pinch the suture 30 and prevent relative movement between the suture retention device 10 and the suture 30 at the pinch point. In this example a protrusion and mating recess are implemented, however, any mechanism that locks the suture 30 to the suture retention device 10 may be implemented.

The suture 30 comprises successively a first length of suture 52 outside the internal chamber 22 extending through the suture exit 32 and a reservoir length of suture 50 within the internal chamber 22 and a second length of suture 53 outside the shell 12 extending through the suture entrance hole 33. As used herein, the term "successively", "successive", and "succession" means following in order in an uninterrupted sequence. As used herein, the term "contiguous" means that the suture sections are continuous and connected without a break. Two severed sutures tied together, for example, are not contiguous. The first length of suture 52 may be contiguous with the reservoir length of suture 50, and the reservoir length of suture 50 may be contiguous with second length of suture 53.

The second length of suture 53, which is a section of suture 30, is free to move to a limited extent through deflection of the spring 26 even though the first length of suture is locked to the shell 12. In other words, when the first length of suture 52 is locked to the shell 12, tension applied to the second length of suture 53 deflects the spring 26 toward the hole 33. A reservoir of suture 50 is within the internal chamber 22 engaging the spring 26, the reservoir of suture 50 being reduced upon placing the suture 30 in tension, the reservoir of suture 50 that leaves the internal chamber 22 becoming part of the second length of suture 53. The reservoir length of suture 50 may slide over the spring 26 during the deflection so that the second length of suture 53 may move relative to the suture retention device 10 even though the shell 12 is locked to the suture 30. The reservoir length of suture 50 is reduced and the second length of suture 53 is lengthened upon placing the suture 30 in tension.

A stop 40 may limit the extent of the resilient movement in one direction along the suture 30 if desired. Friction between the suture 30 and the spring 26 may get very high if the spring gets very close to hole 33. A stop may be prudent to prevent the suture from snapping or fraying. It may also help prevent the suture from slipping over the end of the spring.

An anchor 56 may be attached to the second length of suture 53. The anchor 56 and second length of suture 53 move resiliently toward and away from the shell 12 upon release and application of a force, respectively, with the first length of suture 52 locked to the shell 12.

With a gastropexy, the suture retention device 10 may be located at a position that places tension on the second length of suture 53 and pulls the stomach against the abdominal wall via the anchor 56 but allows some movement in either direction relative to the second length of suture 53 while maintaining tension to allow for changes in thickness in the stomach wall 200 and abdominal wall 202 and/or movement of the anchor 56. The spring 26 maintains tension in the second length of suture 53 by deflecting more or less depending on the force. Movement of the shell 12 relative to the second length of suture 53 reduces or increases the reservoir length of suture 50 inside the internal chamber 22. The reservoir of suture 50 is within the internal chamber 22 connected to the spring 26, the spring 26 being deflected and the reservoir of suture 50 being reduced upon placing the suture 30 in tension.

The spring 26 may be at least one of a crook, a strip, a helical spring, constant force spring, and a clock-spring wound in a spiral pattern. FIGS. 3 and 4 present a crook spring.

Figure 5:
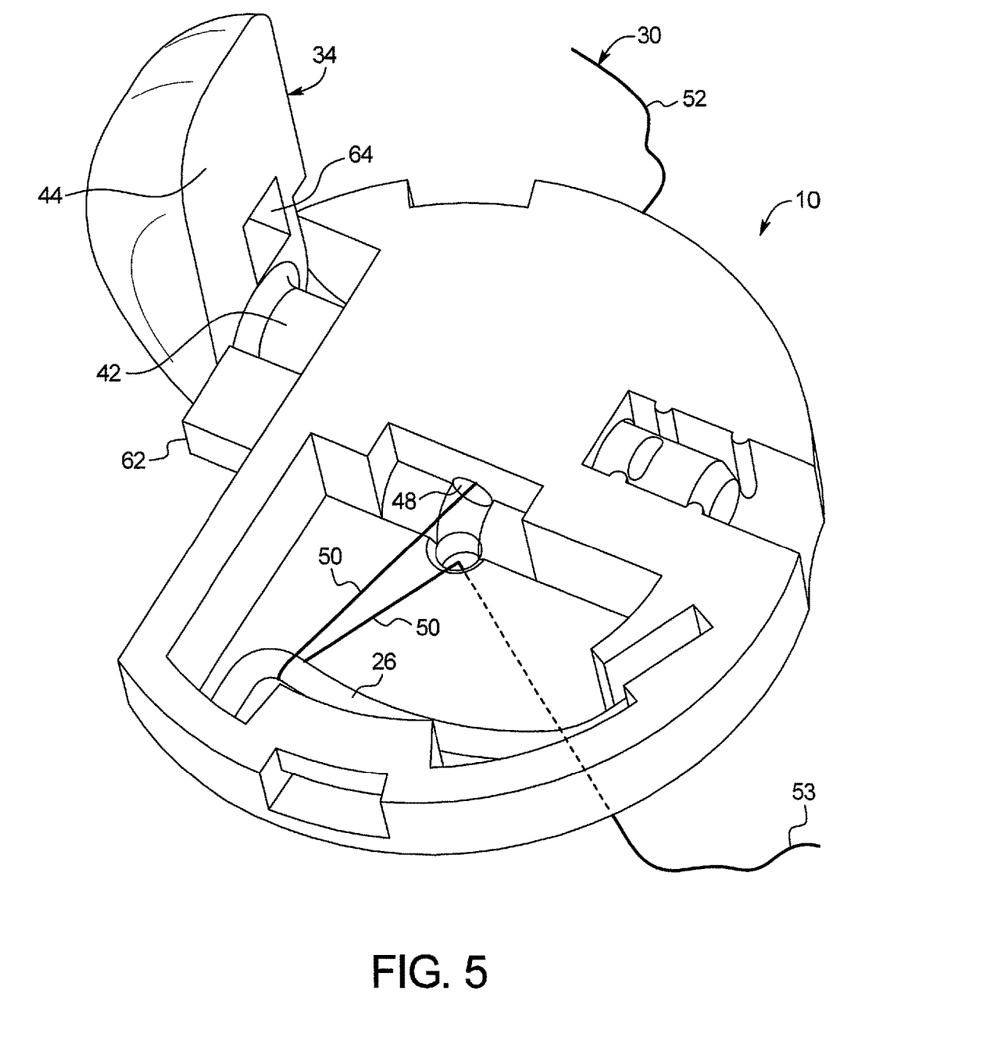
FIG. 5 is a perspective view of another example of a suture retention device having a crook spring in an unlocked configuration, the cap not being shown for the sake of clarity.
Figure 6:
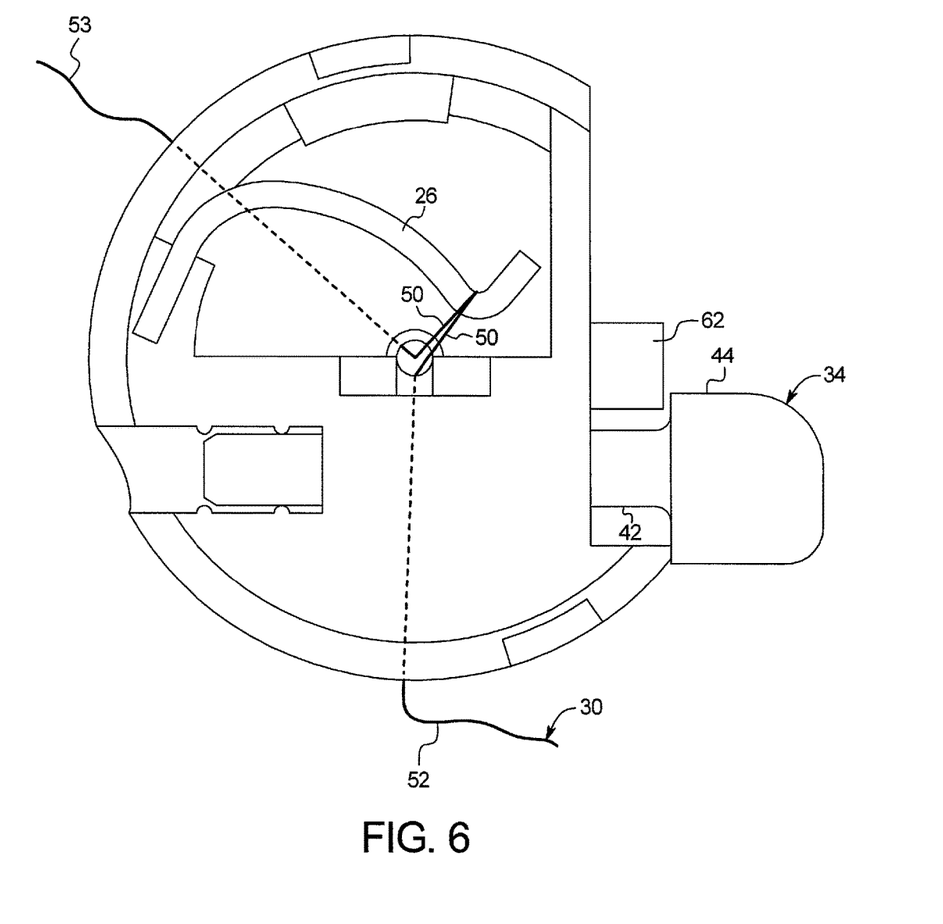
FIG. 6 is a top plan view of the FIG. 5 suture retention device with a spring in a deflected configuration but in an unlocked configuration, the cap not being shown for the sake of clarity.
Figure 7:
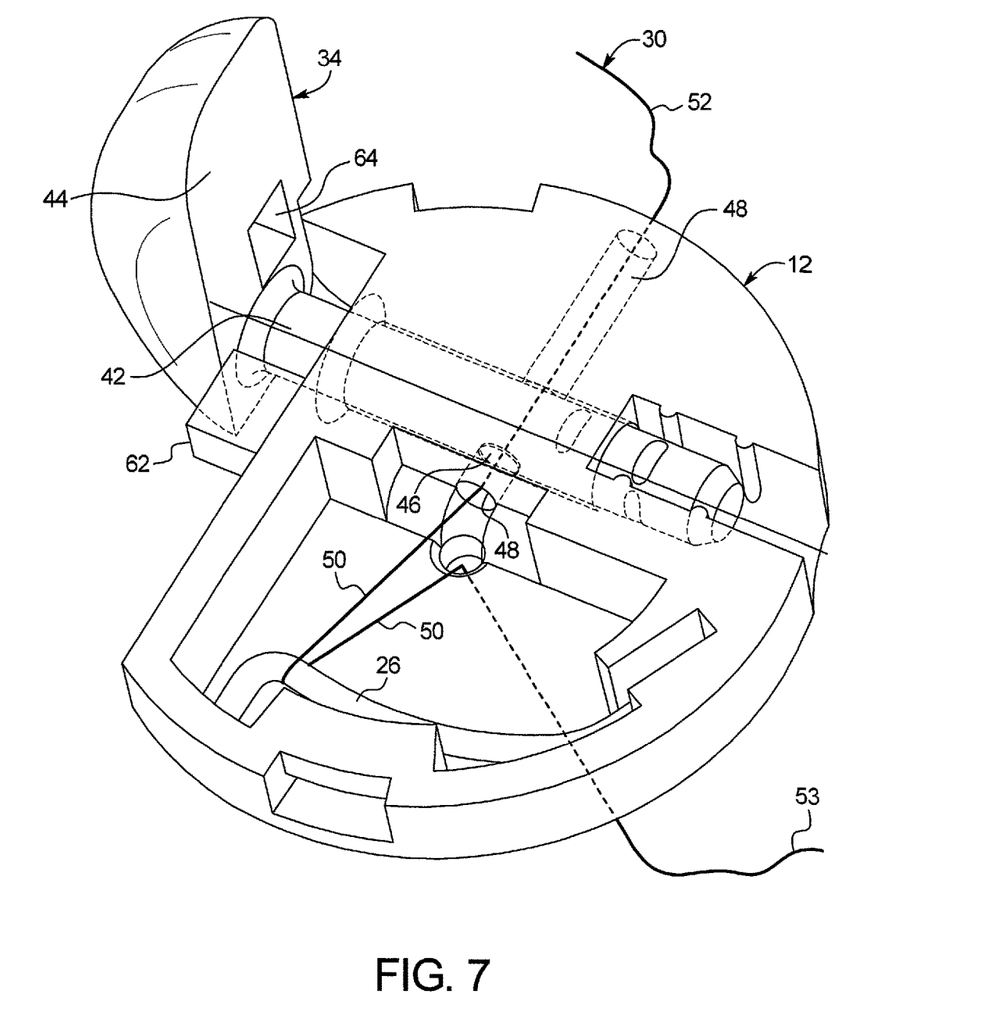
FIG. 7 is a perspective view of the FIG. 5 suture retention mechanism with see-through components, the cap not being shown for the sake of clarity.
Figure 8:
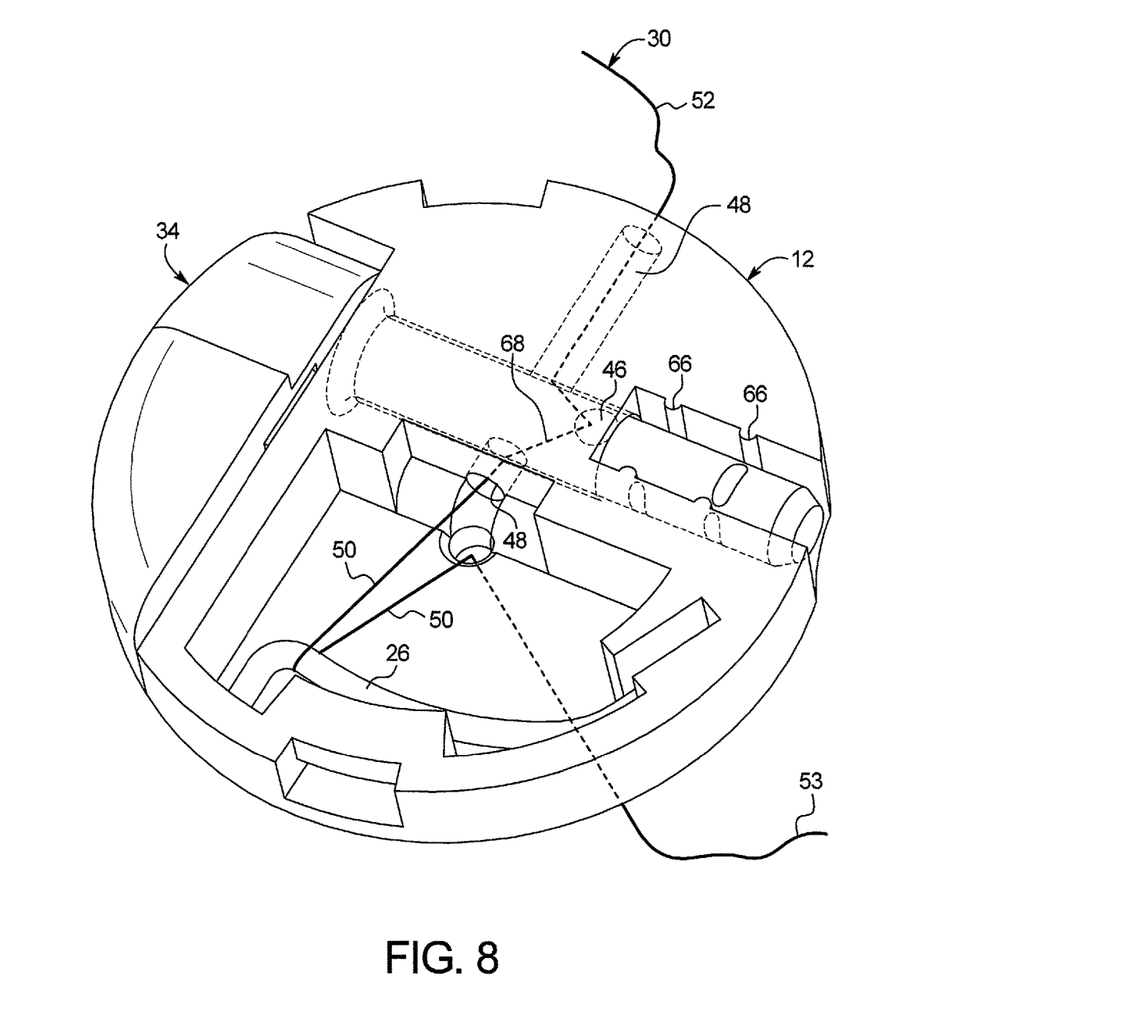
FIG. 8 is a perspective view of the FIG. 5 suture retention mechanism with see-through components in a locked configuration, the cap not being shown for the sake of clarity.

Referring now to FIGS. 5-8, another example of a suture retention device 10 is presented. FIGS. 5, 7 and 8 present perspective views of the suture retention device 10 with the cap 60 removed, and FIG. 6 presents a top view with the cap 60 removed and also shows the spring 26 deflected. The cap 60 is removed to more easily depict the internal workings. In FIGS. 5-7, the lever 44 is shown in an unlocked position. The suture lock 34 comprises a pin 42 and lever 44, the pin 42 having a suture lock hole 46 and the lever 44 attached to the pin 42, the shell 12 having a mating suture lock hole 48 alignable with the suture lock hole 46, the suture 30 passing through the suture lock hole 46 and the mating suture lock hole 48. As shown in FIG. 8, pivoting the lever 44 in one direction rotates the pin 42 causing the suture lock hole 46 and the mating suture lock hole 48 to misalign and lock the suture 30. Pivoting the lever 44 in an opposite direction, back to its original position, rotates the pin 42 to a position wherein the suture lock hole 46 and the mating suture lock hole 48 are aligned and the suture 30 is not locked. In the embodiment presented, the lever 44 is also pressed against the shell 12 when locked. The lever 44 has a protuberance 62 that is received in a recess 64 that prevents the lever 44 from inadvertently rotating to the unlocked position. This is shown in FIG. 8. Detents 66 hold the pin 42 and the lever 44 in place. In this embodiment there is a kink 68 in the suture 30 that increases the pinching force although this is not necessary.

Figure 4A:
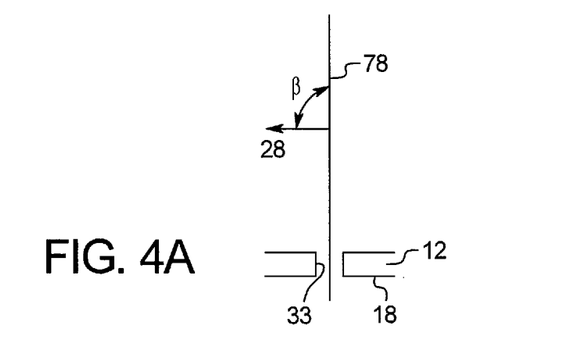
FIG. 4A presents an axis of the device and an example of a spring orientation or deflection relative to the axis.

Referring now to FIG. 4A, the suture entrance hole 33 may define a longitudinal axis 78. If the hole is a cylinder, the axis is the longitudinal axis 78 of the cylinder. Of course the hole may have varying outer circumference shapes, such as a square or polygon, without limitation. In such case, the axis is the longitudinal axis 78 of the hole, similar to what it is for a cylinder. The suture entrance hole 33 is in communication with the internal chamber 22. The spring 26 is mounted within the internal chamber 22 and and is oriented or deflectable transverse to the axis 78 as indicated at 28. The spring may be oriented or deflectable perpendicular to the axis 78. Exactly perpendicular is not necessary as a few degrees variation is possible so, as used herein, "perpendicular" means the angle β may range from 90 degrees to 100 degrees. Up to several degrees variation from perpendicular is also contemplated. For example the orientation or deflection 28 may be transverse, at an angle β of 50 degrees, 60 degrees, 70 degrees, 80 degrees or 90 degrees relative to the axis 78. The angle β of the orientation or deflection 28 relative to the axis 78 may be in the range of 50 degrees to 130 degrees, 60 degrees to 120 degrees, 70 degrees to 110 degrees, and 80 degrees to 100. The orientation or deflection 28 may be toward the suture entrance hole 33 depending on the embodiment. This may be implemented with one or more of the elements of all the examples presented herein.

The suture 30 may have successively a first length of suture 52 outside the shell 12 and a contiguous reservoir length of suture 50 within the internal chamber 12 engaging the spring 26 and a contiguous second length of suture 53 outside the shell 12. The second length of suture 53 passes through the suture exit hole 32 into the internal chamber 22. The shell 12 is resiliently movable relative to the second length of suture 53 by deflecting 28 the spring 26 transverse to the axis 78 thereby reducing the reservoir length of suture 50. This may be implemented with one or more of the elements of all the examples presented herein.

According to a further aspect, a suture retention method is provided comprising locking a suture 30 in a suture retention device 10 such that the suture retention device 10 resiliently moves in either direction along the suture 30 by deflecting a spring 26 while it is locked to the shell 12. As described previously, in one example, there is a first length of suture 52 successive with reservoir length of suture 50 inside the internal chamber 22 that is successive with the second length of suture 53. The reservoir length of suture 50 is connected to the spring 26 so tension on the second length of suture 53 applies tension to the reservoir length of suture 50 and deflects the spring 26. This may be subsequent to locking the first length of suture 52 to the shell 12.

The method may comprise limiting movement of the suture retention device 10 in at least one direction along the suture, for example by stop 40. The suture lock device 10 may be moved by unlocking the suture 30, repositioning the suture retention device 10 along the suture 30 and re-locking the suture 30 in the suture retention device 10. The method may also comprise resiliently moving the locked suture retention device 10 along the suture 30 under tension. As described previously, the suture retention device 10 may be moved resiliently a limited distance along the suture 30 under tension. The reservoir length of suture 50 may be reduced within the internal chamber 22 by placing the suture 30 in tension. The method may also comprise a reservoir length of suture 50 within the internal chamber 22 connected to the spring 26 and deflecting the spring 26 thereby reducing the reservoir length of suture 50 upon placing the suture 30 in tension, the reservoir length of suture 50 sliding over the spring 26.

Figure 9:
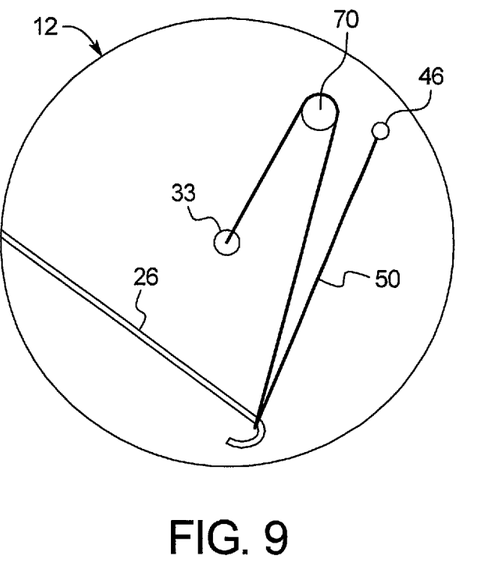
FIG. 9 presents a top schematic view of a further example of a suture retention device in an unlocked configuration and having a crook spring, the cap not being shown for the sake of clarity.
Figure 10:
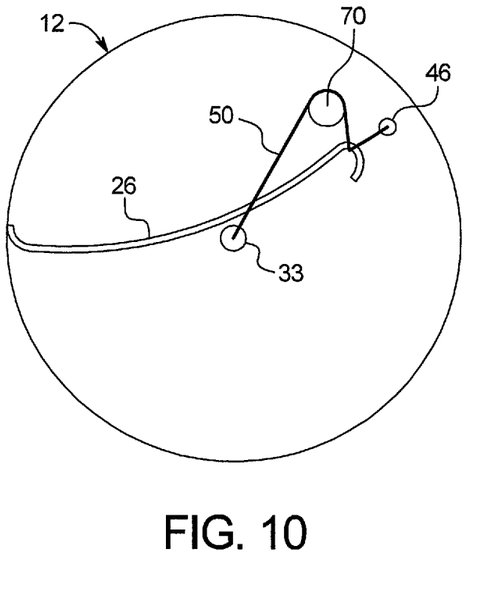
FIG. 10 presents a top schematic view of the FIG. 9 suture retention device with the spring deflected, the cap not being shown for the sake of clarity.

Referring now to FIGS. 9 and 10 another example is presented that is similar to the examples already described. In this example, there is a post or pulley 70 around which the reservoir length of suture 50 passes. As is apparent from the figures, this embodiment increases the reservoir length of suture 50. Placing the suture 30 in tension pulls the spring 26 toward the post 70 and the spring 26 may be deflected to a greater degree because it is pulled toward the post 70 on the far side of the shell 12. The post 70 may be configured as a pulley or some other structure that facilitates the suture passing around it. At least one of the upper surface 14 and lower surface 18 may have a suture entrance hole 33 and include a post or pulley 40 around which the reservoir length of suture 50 passes thereby increasing the reservoir length of suture 50, and wherein deflecting the spring 26 reduces the reservoir length of suture 50 by pulling the spring 26 toward the post or pulley 40 such that the spring 26 is deflected past the suture entrance hole 33.

Figure 11:
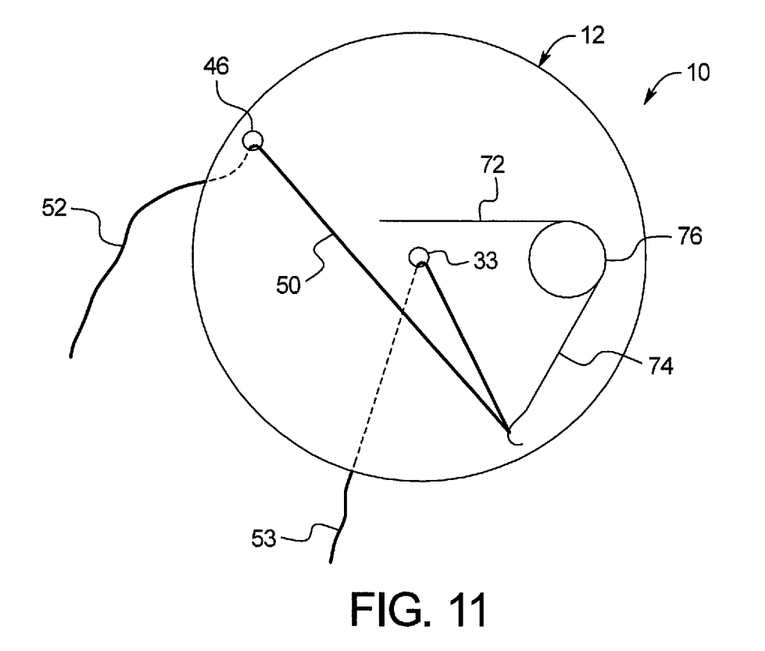
FIG. 11 presents a top schematic view of another example of a suture retention device implementing a helical spring, the cap not being shown for the sake of clarity.
Figure 12:
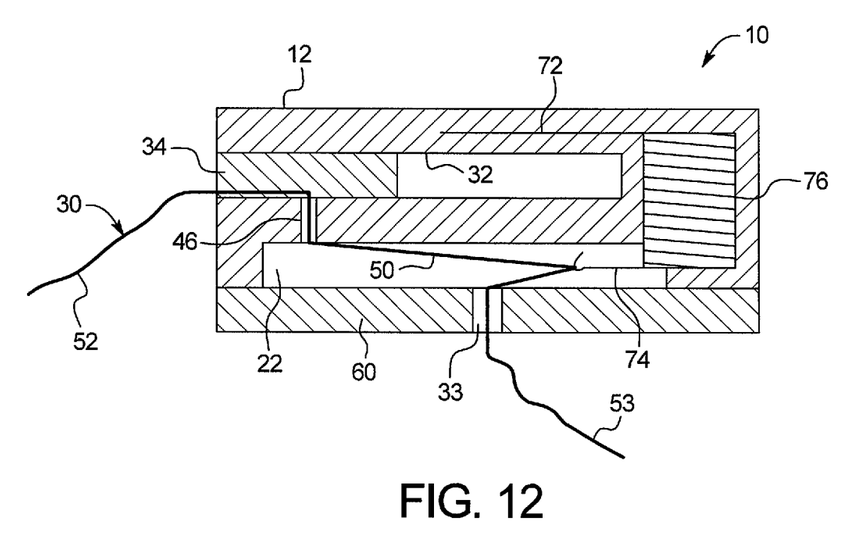
FIG. 12 presents a side cross-sectional view of the FIG. 11 device in a locked configuration.
Figure 13:
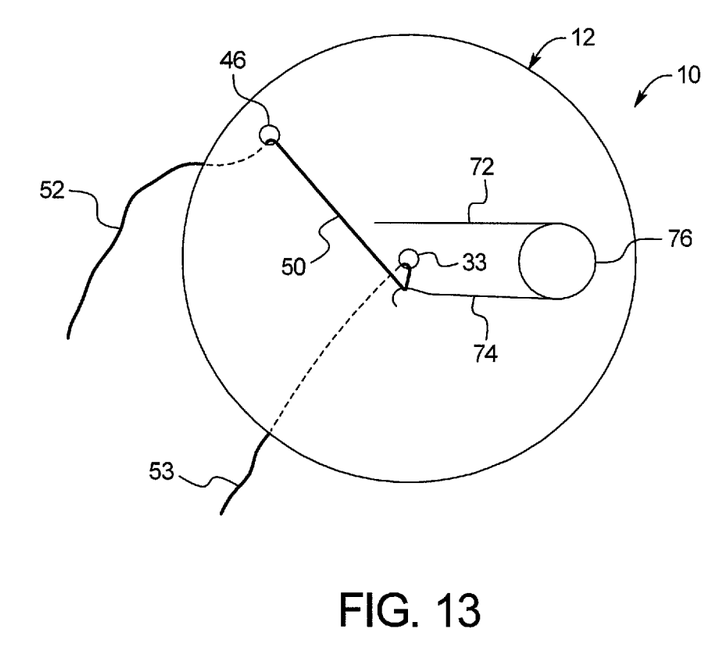
FIG. 13 presents a top schematic view of the FIG. 11 device having a helical spring shown in a deflected configuration.

Referring now to FIGS. 11-13 an example of a suture retention device 10 having a helical spring 76 is presented. The helical spring 76 has a first arm 72 and a second arm 74. The cap 60 is not shown in FIGS. 10 and 12 in order to show the internal workings. The first arm 72 is locked to the shell 12. The second arm 74 is free to move within the cavity 22 and is connected to the reservoir length of suture 50. The principal of operation is the same as described in previous examples. FIG. 11 presents the suture lock device 10 in an unlocked configuration, and FIGS. 12 and 13 presents the suture lock device 10 in a locked configuration.

Dimensions of the suture lock device 10 vary depending on the application. For a gastropexy for example the diameter may by 10-20 mm and the thickness may be 4-8 mm and at full deflection of the spring the spring force may range from 0.5 Newtons to 7 Newtons. For another application the diameter and thickness may be larger or smaller and spring force may be larger or smaller. As force increases the diameter may tend to increase to accommodate the greater load.

The shell 12 may be plastic such as ABS (acrylonitrile-butadiene-styrene), polyethylene, acetal, or a metal, or other materials with suitable stiffness. The spring 26 may be nitinol or spring steel or other material having suitable springiness. The suture may be non-absorbable such as silk, synthetic fiber, nylon, polypropylene or other suitable suture material, it may also be absorbable, collagen for example or other suitable material.

Various currently contemplated examples follow:

EXAMPLE 1

With reference to FIGS. 1-13, a suture retention device is presented comprising a shell such as shell 12 having a thickness such as thickness 14 and an upper surface such as upper surface 16 and a lower surface such as lower surface 18 spaced apart by the thickness 14, the shell 12 having an outer diameter such as outer diameter 20 that is greater than the thickness 14, the shell 12 defining an internal chamber such as internal chamber 22, the lower surface having a suture entrance hole; a spring such as spring 26 mounted within the internal chamber 22; and a suture such as suture 30 having in succession a first length of suture such as first length of suture 52 outside the shell 12 and a reservoir length of suture such as reservoir length of suture 50 within the internal chamber 12 engaging the spring 26 and a second length of suture such as second length of suture 53 outside the shell 12, the shell 12 being movable relative to the second length of suture 53 by deflecting the spring 26 and reducing the reservoir length of suture 50; and an anchor 56 attached to the second length of suture 53.

EXAMPLE 2

The suture retention device 10 of Example 1, wherein the spring engages a stop such as stop 40 that limits reducing the reservoir length of suture 50. This may be implemented with the elements of Examples 3 through 21 alternatively or in addition to one another.

EXAMPLE 3

The suture retention device 10 of Example 1, wherein the spring 26 is at least one of a crook, a strip, a helical spring, a constant force spring, and a clock-spring wound in a spiral pattern. This may be implemented with the elements of Example 2 and Examples 4 through 21 alternatively or in addition to one another.

EXAMPLE 4

The suture retention device 10 of Example 1, wherein the first length of suture 52 is locked to the shell 12. This may be implemented with the elements of Examples 2 and 3 and Examples 5 through 21 alternatively or in addition to one another.

EXAMPLE 5

The suture retention device 10 of Example 1, wherein deflecting the spring 26 reduces the reservoir length of suture 50. This may be implemented with the elements of Examples 2 through 4 and 6 through 21 alternatively or in addition to one another.

EXAMPLE 6

The suture retention device 10 of Example 1, wherein the suture entrance hole 33 defines a longitudinal axis 78 and the spring 26 is oriented or deflects perpendicular to the longitudinal axis 78. This may be implemented with the elements of Examples 2 through 5 and 7 through 21 alternatively or in addition to one another.

EXAMPLE 7

The suture retention device 10 of Example 1, wherein the reservoir length of suture 50 engages the spring 26 in a manner that allows the reservoir length of suture 50 to slide over the spring 26. This may be implemented with the elements of Examples 2 through 6 and 8 through 21 alternatively or in addition to one another.

EXAMPLE 8

The suture retention device 10 of Example 1, including a post or pulley such as post or pulley 40 around which the reservoir length of suture 50 passes thereby increasing the reservoir length of suture 50, and wherein deflecting the spring 26 reduces the reservoir length of suture 50 by pulling the spring 26 toward the post or pulley 40 such that the spring 26 is deflected past the suture entrance hole 33. This may be implemented with the elements of Examples 2 through 7 and 9 through 21 alternatively or in addition to one another.

EXAMPLE 9

The suture retention device 10 of Example 1, wherein the suture entrance hole 33 is at the center of the lower surface with the second length of suture 53 passing through the suture entrance hole 33 and the shell 12 has a suture exit hole 32 with the first length of suture 52 passing through the suture exit hole 32. This may be implemented with the elements of Examples 2 through 8 and 10 through 21 alternatively or in addition to one another.

EXAMPLE 10

The suture retention device 10 of Example 1 wherein placing the suture 30 in tension causes the spring 26 to deflect toward the suture entrance hole 33. This may be implemented with the elements of Examples 2 through 9 and 11 through 21 alternatively or in addition to one another.

EXAMPLE 11

The suture retention device 10 of Example 1, wherein the spring 26 mounted within the internal chamber 22 engages the suture 30 and applies a force to the suture 30 upon deflection toward the suture entrance hole 33. This may be implemented with the elements of Examples 2 through 10 and 12 through 21 alternatively or in addition to one another.

EXAMPLE 12

The suture retention device 10 of Example 1, wherein the suture lock 34 comprises a pin such as pin 42 and lever such as lever 44, the pin 42 having a suture lock hole such as suture lock hole 46 and the lever 44 attached to the pin 42, the shell 12 having a mating suture lock hole such as mating suture lock hole 48 alignable with the suture lock hole 46, the suture 30 passing through the suture lock hole 46 and the mating suture lock hole 48, wherein pivoting the lever 44 in one direction rotates the pin 42 causing the suture lock hole 46 and the mating suture lock hole 48 to misalign and lock the suture 30, and pivoting the lever 44 in an opposite direction rotates the pin 42 to a position wherein the suture lock hole 46 and the mating suture lock hole 48 are aligned and the suture 30 is not locked. This may be implemented with the elements of Examples 2 through 11 and 13 through 21 alternatively or in addition to one another.

EXAMPLE 13

A method of retaining a suture 30 with a suture retention device 10, the suture retention device 10 comprising a shell such as shell 12 having an internal chamber such as internal chamber 22, a suture such as suture 30 in succession having a first length of suture 52 outside the shell 12 and a reservoir length of suture 50 within the internal chamber 22 that engages a spring such as spring 26 and a second length of suture 53 outside the shell 12, the method comprising: locking the first length of suture 52 to the shell 12; and moving the shell 12 relative to the second length of suture 53 by deflecting the spring 26 and reducing the reservoir length of suture 50.

EXAMPLE 14

The suture retention method of Example 13, comprising resiliently moving the shell 12 in either direction along the second length of suture 53. This may be implemented with the elements of Examples 15 through 21 alternatively or in addition to one another.

EXAMPLE 15

The suture retention method of Example 13, comprising limiting movement of the shell 12 in at least one direction along the second length of suture 53. This may be implemented with the elements of Examples 14 and 16 through 21 alternatively or in addition to one another.

EXAMPLE 16

The suture retention method of Example 13, comprising unlocking the suture 30, repositioning the shell 12 along the suture 30 and re-locking the suture 30 in the shell 12. This may be implemented with the elements of Examples 14 through 15 and Examples of 17 through 21 alternatively or in addition to one another.

EXAMPLE 17

The suture retention method of Example 13, wherein at least one of the upper surface 16 and lower surface 18 has a suture entrance hole 33 at its center with the second length of suture 53 passing through the suture entrance hole 33. This may be implemented with the elements of Examples 15 through 16 and 18 through 21 alternatively or in addition to one another.

EXAMPLE 18

The suture retention method of Example 13 wherein the second length of suture 53 is attached to an anchor such as anchor 56. This may be implemented with the elements of Examples 14 through 17 and 19 through 21 alternatively or in addition to one another.

EXAMPLE 19

The suture retention method of Example 13, comprising reducing the reservoir length of suture 50 within the internal chamber 22 and reducing the reservoir length of suture 50 by placing the suture in tension. This may be implemented with the elements of Examples 14 through 18 and 21 alternatively or in addition to one another.

EXAMPLE 20

The suture retention method of Example 13, comprising deflecting the spring 26 thereby reducing the reservoir length of suture 50 upon placing the suture 30 in tension, the reservoir length of suture 50 sliding over the spring 26. This may be implemented with the elements of Examples 14 through 19 and 21 alternatively or in addition to one another.

EXAMPLE 21

With reference to FIGS. 1-13, a suture retention device is presented comprising a shell such as shell 12 having a thickness such as thickness 14 and an upper surface such as upper surface 16 and a lower surface such as lower surface 18 spaced apart by the thickness 14, the shell 12 having an outer diameter such as outer diameter 20 that is greater than the thickness 14, the shell 12 defining an internal chamber such as internal chamber 22, the lower surface 18 having a suture entrance hole such as suture entrance hole 33 at its center, the suture entrance hole 33 being in communication with the internal chamber 22 and defining a longitudinal axis; a spring such as spring 26 mounted within the internal chamber 22 and deflectable perpendicular to the axis 78; and a suture such as suture 30 having in succession a first length of suture such as first length of suture 52 outside the shell 12 and a reservoir length of suture such as reservoir length of suture 50 within the internal chamber 12 engaging the spring 26 and a second length of suture such as second length of suture 53 outside the shell 12, the second length of suture 53 passing through the suture entrance hole 33 into the internal chamber 22, the shell 12 being resiliently movable relative to the second length of suture 53 by deflecting the spring 26 perpendicular to the axis 78 thereby reducing the reservoir length of suture 50. This may be implemented with the elements of Examples 1 through 20 alternatively or in addition to one another.

All features and modifications of the described examples and dependent claims are usable in all aspects of the examples taught herein. Furthermore, the individual features of the dependent claims, as well as a; features and modifications of the described examples are combinable and interchangeable with one another.

What is claimed is:

1. A suture retention device, comprising:
    a shell having a thickness and an upper surface and a lower surface spaced apart by the thickness, the shell having an outer diameter that is greater than the thickness, the shell defining an internal chamber, the lower surface having a suture entrance hole;
    a spring mounted within the internal chamber;
    a suture having in succession a first length of suture outside the shell and a reservoir length of suture within the internal chamber engaging the spring and a second length of suture outside the shell, the shell being movable relative to the second length of suture by deflecting the spring and reducing the reservoir length of suture; and,
    an anchor attached to the second length of suture;
    wherein the suture entrance hole is at the center of the lower surface with the second length of suture passing through the suture entrance hole and the shell has a suture exit hole with the first length of suture passing through the suture exit hole.

2. The suture retention device of claim 1, wherein the spring engages a stop that limits reducing the reservoir length of suture.

3. The suture retention device of claim 1, wherein the spring is at least one of a crook, a strip, a helical spring, a constant force spring, and a clock-spring wound in a spiral pattern.

4. The suture retention device of claim 1, wherein the first length of suture is locked to the shell.

5. The suture retention device of claim 1, wherein the suture entrance hole defines a longitudinal axis and the spring is oriented or deflects perpendicular to the axis.

6. The suture retention device of claim 1, wherein the reservoir length of suture engages the spring in a manner that allows the reservoir length of suture to slide over the spring.

7. The suture retention device of claim 1, comprising a post or pulley around which the reservoir length of suture passes thereby increasing the reservoir length of suture, and wherein deflecting the spring reduces the reservoir length of suture by pulling the spring toward the post or pulley such that the spring is deflected past the suture entrance hole.

8. The suture retention device of claim 1, wherein placing the suture in tension causes the spring to deflect toward the suture entrance hole.

9. The suture retention device of claim 1, wherein the spring mounted within the internal chamber engages the suture and applies a force to the suture upon deflection toward the suture entrance hole.

10. The suture retention device of claim 1, comprising a suture lock connected to the shell, the suture lock comprising a pin and lever, the pin having a suture lock hole and the lever attached to the pin, the shell having a mating suture lock hole alignable with the suture lock hole, the suture passing through the suture lock hole and the mating suture lock hole, wherein pivoting the lever in one direction rotates the pin causing the suture lock hole and the mating suture lock hole to misalign and lock the suture, and pivoting the lever in an opposite direction rotates the pin to a position wherein the suture lock hole and the mating suture lock hole are aligned and the suture is not locked.

11. A method of retaining a suture with a suture retention device, the suture retention device comprising a shell having an upper surface, a lower surface, an internal chamber, a suture in succession having a first length of suture outside the shell and a reservoir length of suture within the internal chamber that engages a spring and a second length of suture outside the shell,
    the method comprising:
    locking the first length of suture to the shell;
    moving the shell relative to the second length of suture by deflecting the spring and reducing the reservoir length of suture; and
    unlocking the suture, repositioning the shell along the suture and re-locking the suture in the shell.

12. The suture retention method of clam 11, comprising resiliently moving the shell along the second length of suture.

13. The method of claim 11, comprising limiting movement of the shell in at least one direction along the second length of suture.

14. The suture retention method of claim 11, wherein at least one of the upper surface and lower surface has a suture entrance hole at its center with the second length of suture passing through the suture entrance hole.

15. The suture retention device of claim 11 wherein the second length of suture is attached to an anchor.

16. The suture retention method of claim 11, comprising reducing the reservoir length of suture within the internal chamber and reducing the reservoir length of suture by placing the suture in tension.

17. The suture retention method of claim 11, comprising deflecting the spring thereby reducing the reservoir length of suture upon placing the suture in tension, the reservoir length of suture sliding over the spring.

\* \* \* \* \*